United States Patent
Donawick (10) Patent No.: US 8,328,759 B2
(45) Date of Patent: Dec. 11, 2012

(54) INTRALUMINAL CANNULA PLACEMENT APPARATUS UTILIZING A SPECIALIZED CANNULA FOR USE WITH A PREVIOUSLY INSERTED I.V. CATHETER

(76) Inventor: William Joseph Donawick, West Chester, PA (US)

( * ) Notice: Subject to any disclaimer, the term of this patent is extended or adjusted under 35 U.S.C. 154(b) by 305 days.

(21) Appl. No.: 12/855,823

(22) Filed: Aug. 13, 2010

(65) Prior Publication Data
US 2012/0041392 A1 Feb. 16, 2012

(51) Int. Cl.
*A61M 5/178* (2006.01)
(52) U.S. Cl. .................................. 604/164.01
(58) Field of Classification Search .................. 604/158, 604/164.01
See application file for complete search history.

(56) References Cited

U.S. PATENT DOCUMENTS

| | | |
|---|---|---|
| 3,515,137 A | 6/1970 | Santomieri |
| 3,633,579 A | 1/1972 | Alley et al. |
| 4,068,659 A | 1/1978 | Moorehead |
| 4,068,660 A | 1/1978 | Beck |
| 4,205,675 A | 6/1980 | Vaillancourt |
| 4,235,232 A | 11/1980 | Spaven et al. |
| 4,327,723 A | 5/1982 | Frankhouser |
| 4,366,817 A | 1/1983 | Thomas |
| 4,387,879 A | 6/1983 | Tauschinski |
| 4,613,329 A | 9/1986 | Bodicky |
| 4,634,433 A | 1/1987 | Osborne |
| 4,687,470 A | 8/1987 | Okada |
| 4,696,296 A | 9/1987 | Palmer |
| 4,758,225 A | 7/1988 | Cox et al. |
| 4,767,409 A | 8/1988 | Brooks |
| 4,834,710 A | 5/1989 | Fleck |
| 4,913,704 A | 4/1990 | Kurimoto |
| 5,015,239 A | 5/1991 | Browne |
| 5,064,416 A | 11/1991 | Newguard et al. |
| 5,080,654 A | 1/1992 | Picha et al. |
| 5,120,324 A | 6/1992 | Sancoff |
| 5,242,423 A | 9/1993 | Goodsir |
| 5,476,451 A | 12/1995 | Ensminger |
| 5,478,331 A | 12/1995 | Heflin et al. |
| 5,830,189 A | 11/1998 | Chang |
| 5,843,046 A | 12/1998 | Motisi et al. |
| 5,855,566 A | 1/1999 | Dunlap et al. |
| 5,925,005 A | 7/1999 | May |
| 5,967,490 A | 10/1999 | Pike |
| 5,992,899 A | 11/1999 | Strowe |
| 5,993,437 A | 11/1999 | Raoz |
| 6,156,016 A | 12/2000 | Maginot |

(Continued)

*Primary Examiner* — Kevin C Sirmons
*Assistant Examiner* — Bradley Osinski
(74) *Attorney, Agent, or Firm* — Laurence A. Weinberger (57) ABSTRACT

A specialized cannula and intraluminal cannula placement apparatus allow the insertion of an intraluminal cannula through a previously inserted standard I.V. catheter so that the intraluminal cannula extends beyond the end of a standard catheter. By using an intraluminal cannula of appropriate length, the intraluminal cannula may be used to bypass a flexure-caused obstruction in a vein during the administration of fluids in patients who are unable to cooperate with medical or veterinary procedures, most particularly with human infants, geriatric patients, and animals. Use of the specialized cannula and intraluminal cannula placement apparatus does not require removal of the previously placed I.V. catheter. The exterior diameter of the specialized cannula has a smaller diameter than the interior diameter of the previously placed standard I.V. catheter. A specially adapted seal seals the space between the inserted specialized cannula and a standard Luer hub of an I.V. catheter. In use, a health practitioner advances the specialized cannula through the standard I.V. catheter and into the vein with a pusher. When inserted, there is no extracorporeal extension to the hub of the standard I.V. catheter and the intraluminal cannula cannot be removed without simultaneous removal of the standard I.V catheter.

32 Claims, 11 Drawing Sheets

U.S. PATENT DOCUMENTS

| | | |
|---|---|---|
| 6,159,198 A | 12/2000 | Gardeski et al. |
| 6,171,281 B1 | 1/2001 | Zhang |
| 6,235,001 B1 | 5/2001 | O'Holloran et al. |
| 6,245,029 B1 | 6/2001 | Fujita et al. |
| 6,413,244 B1 | 7/2002 | Bestetti et al. |
| 6,485,473 B1 | 11/2002 | Lynn |
| 6,506,182 B2 | 1/2003 | Estabrook |
| 6,558,354 B1 | 5/2003 | Howell |
| 6,572,571 B2 | 6/2003 | Lowe |
| 6,592,553 B2 | 7/2003 | Zhang et al. |
| 6,610,045 B2 | 8/2003 | Chavez et al. |
| 6,740,063 B2 | 5/2004 | Lynn |
| 6,752,800 B1 | 6/2004 | Winston et al. |
| 6,786,891 B2 | 9/2004 | Hiejima |
| 7,008,404 B2 | 3/2006 | Nakajima |
| 7,048,711 B2 | 5/2006 | Rosenman et al. |
| 7,137,654 B2 | 11/2006 | Segal et al. |
| 7,156,836 B2 | 1/2007 | Teo |
| 7,306,198 B2 | 12/2007 | Doyle |
| 7,318,818 B2 | 1/2008 | Yashiro et al. |
| 7,377,909 B2 | 5/2008 | Rickerd |
| 2002/0072712 A1 | 6/2002 | Nool |
| 2005/0137527 A1 | 6/2005 | Kunin |
| 2006/0116629 A1 | 6/2006 | Tal |
| 2007/0100295 A1 | 5/2007 | Belley et al. |
| 2008/0033396 A1 | 2/2008 | Banek |

INTRALUMINAL CANNULA PLACEMENT APPARATUS UTILIZING A SPECIALIZED CANNULA FOR USE WITH A PREVIOUSLY INSERTED I.V. CATHETER

BACKGROUND

1. Field of the Invention

This invention relates to catheters placed in the veins or arteries of animals and humans for the continuous transmission of fluids. Often catheters become unusable due to blockage of the vein or artery distal to the tip of the inserted catheter. The present invention consists of a specialized cannula and associated intraluminal cannula placement apparatus for inserting the specialized cannula into and through the lumen (hollow center cavity) of a previously inserted standard I.V. catheter so that the tip of the specialized cannula extends substantially beyond the tip of the catheter to beyond a point of blockage.

2. Description of the Prior Art

In medical and veterinary practice it is common procedure to provide fluids and medications to patients through a catheter. The typical catheter used today has a female Luer fitting (standard I.V. catheter hub) on the proximal end to which fluid lines or medication introducing devices can be attached. The catheter is typically inserted into a vein in the hand, forearm, or forelimb in humans and in domestic cats, dogs, or other companion and domesticated animals. Often fluids are administered through the cephalic vein, a large superficial vein in the forelimb running from the hand or paw to the shoulder. The injection site is generally on the anterior surface of the limb, between the carpals and the elbow joint. However, depending on the circumstances, the catheter may be introduced in other areas. Puncturing of the skin for placement of the catheter is accomplished by a sharpened needle located inside the catheter that protrudes beyond the tip of the catheter. Even in skilled hands, the insertion of the catheter is not without some discomfort to the patient and can be traumatic especially in young and old human patients and in animals of any age. Since catheters are usually placed away from the first major limb joint, constriction of the vein or artery and obstructions to blood flow on the heart side of the catheter insertion point can occur if the joint is flexed and kept in a flexed position for any length of time. Continued flexion is more common in young and old human patients and in sedated animals that do not move around. Constriction may also occur due to other circumstances. When this occurs, prescribed fluid or medicant administration is interrupted. If occlusion of a vein persists, the catheter may become clotted and prevent further treatment.

When constriction seriously impedes the flow of fluid through the catheter, typical remedies are either to apply an external splint to restrict movement of the offending joint, to withdraw the catheter and replace it with another longer catheter more resistant to constriction/obstruction, or to withdraw the catheter and insert a new catheter above the point of constriction. The accompanying pain/discomfort of the replacement procedure, especially if locating the vein or artery proves difficult, makes an alternative procedure desirable. The specialized cannula and intraluminal cannula placement apparatus of the present invention alleviates the need for placement of a new catheter by providing a mechanism for the fluid tight insertion into and through the previously inserted catheter of a specialized cannula that is sufficiently long to bypass the point of constriction. The specialized cannula has an outside diameter that is smaller than the inside diameter of the standard I.V. catheter which allows the specialized cannula to be slidingly inserted through the catheter. For this reason, the specialized cannula is referred to as an intraluminal cannula. Despite the reduced diameter of the specialized cannula, sufficient flow of fluids for medical treatment can be maintained. As will be described in greater detail below, after insertion of the specialized cannula, the cannula placement assembly is detached and standard fluid lines or medication delivering devices can be fastened to the standard I.V. catheter hub as before. None of the prior art patents teaches the solution provided by the present invention.

In U.S. Pat. No. 7,156,836, Teo teaches a double cannula assembly that is used to overcome the problem of clotting within a cannula. In this invention, an outer cannula previously placed in a vein has inserted into it a smaller diameter inner cannula. The contacting surfaces between the outer surface of the inner cannula and the inner surface of the outer cannula provide a sliding tight fit which is sufficient to allow insertion of the inner cannula but tight enough to prevent blood or other fluids from seeping between the two surfaces. Since clots frequently form at the tip of the cannula, removing and inserting an inner cannula displaces the clot and reopens the passageway. When clotting occurs, the inner cannula is removed, leaving the outer cannula in place. If desired, a new inner cannula may then be inserted through the outer cannula.

In U.S. Pat. No. 3,633,579, Alley, teaches a device for placing an inner catheter within a cannula that has been previously inserted with a needle. A tapered locking ferrule coaxial with and surrounding the catheter is used to secure the catheter to the previously placed cannula. The ferrule is slid along the catheter until the distal end of the tapered ferrule enters a tapered proximal opening in the rear of the cannula. The ferrule is made of a softer material than that of the previously placed cannula, so that the ferrule may be wedged into the cannula taper, said wedging action causing the ferrule to constrict and grip the outer surface of the catheter thereby locking the catheter against axial movement relative to the cannula. The previously placed cannula does not have a standard I.V. catheter Luer lock at the rear end, and therefore, the previously placed cannula is incapable of attaching to the Luer lock of another cannula placement device.

In U.S. Pat. No. 3,515,137, Santomieri teaches a catheter unit using one cannula, which is placed using a leading needle and an inserter. The inserter is coaxial with the cannula, surrounds the cannula, and is made of a resiliently compressible material. Compressing the inserter grips the cannula and needle for insertion. After puncture and insertion, the grip on the inserter is loosened so that the needle may be withdrawn. The inserter can then be used to grip just the cannula to advance the cannula further into the vein. Repeatedly using the inserter to grip the cannula to advance it forward, and then loosening the cannula and sliding it towards the end of the cannula enables the user to advance the cannula as far as is desired into correct position within the body.

U.S. Pat. No. 4,235,232 by Spaven et al. teaches a hub device for use with catheter placement where the catheter is inserted through a dimple in the elastomeric material of the hub, which forms a seal around the catheter.

U.S. Pat. No. 4,613,329 by Bodicky teaches a catheter placement device with an elastomeric grommet with bore, through which the catheter is placed, said grommet permitting relatively low resistance to distal movement of the catheter and relatively high resistance to proximal movement of the catheter.

U.S. Pat. No. 4,068,659 by Moorehead and U.S. Pat. No. 4,068,660 by Beck teach a sterilizable disposable assembly for inserting a catheter into a vein wherein the catheter is located inside the needle and connected sheath during insertion. After insertion, pressure is applied to the skin above the insertion site to capture/hold the catheter in the vein while the needle is withdrawn. The trailing end of the catheter is pushed out of the sheath by the advancement of the leading edge of an inserter, which can be advanced by a handle protruding out of the sheath. The inserter has attached a stiffener, smaller in diameter and coaxial with the catheter, that extends substantially the length of the catheter. The stiffener is attached at the leading edge of the inserter and keeps the catheter from unduly flexing during insertion but is otherwise not attached to the catheter. The catheter placement assembly is discarded following placement of the catheter.

U.S. Pat. No. 4,205,675 by Vaillancourt teaches a catheter placement unit that is used with an introducer needle and introducer catheter. The catheter placement unit contains a connector with an internal bore and a male fitting for coupling to the catheter fitting to create a connection.

U.S. Pat. No. 4,634,433 by Osborne teaches a flexible sheath assembly for protecting the sterility of the exposed portion of a catheter, where the unexposed portion has been placed in a vein. When it is necessary to adjust the depth of insertion of the catheter, the flexible sheath assembly encasing the exposed portion of the catheter preserves the sterility of the catheter so that the depth of insertion can be adjusted without causing contamination. U.S. Pat. No. 4,767,409 by Brooks and U.S. Pat. No. 4,834,710 by Fleck similarly teach devices for protecting a catheter from contamination during and after placement in a vein.

U.S. Pat. No. 6,156,016 by Maginot teaches a catheter system comprising a guide catheter with guide lumen extending between a distal guide orifice and a proximal guide orifice. The catheter system also includes an original catheter within the guide lumen of the guide catheter. In addition, the system features a replacement catheter within the guide lumen of the guide catheter.

U.S. Patent Application Publication 2006/0116629 A1 by Tal et al. teaches a catheter insertion apparatus with a catheter featuring a first and second lumen. A first member moves within the first lumen to create a cavity, and a second member moves within the second lumen. Furthermore, the cavity created by the first member is designed for movement of the second member.

U.S. Patent Application Publication 2007/0100295 by Belley et al. teaches a device for use with catheter apparatus that features an internal seal.

BRIEF DESCRIPTION OF THE DRAWINGS

The preferred embodiments of the invention are illustrated in the drawings in which like reference numbers refer to like elements.

DETAILED DESCRIPTION OF THE INVENTION

Definitions

For clarity of description in this patent document, the following definitions apply:

"PROXIMAL" refers to a location on a device or a component that is closest to the practitioner when the device or component is used with a patient.

"DISTAL" refers to a location on a device or a component that is farthest from the practitioner when the device or component is used with a patient.

"PRACTITIONER" is generally inclusive of veterinarians, physicians, clinicians, surgeons, medical or veterinary technicians, nurses, lab technicians, and like personnel.

"PATIENT" includes both humans and animals that are undergoing medical procedures.

MODIFIED MALE LUER ADAPTER" refers to a male Luer hub having the characteristics described in this patent document.

"STANDARD I.V. CATHETER HUB" refers to an industry standard female Luer lock hub attached to a semi-rigid I.V. tube, which may be of various gauges and length.

"CATHETER" shall mean a tube attached to a STANDARD I.V. CATHETER HUB that is introduced through the skin and into a vein or artery. This tube may also be referred to in the literature as a "cannula", but in order to distinguish this tube from the intraluminal tube inserted by the device of the present invention, the term CATHETER will be used in this patent document.

"SPECIALIZED CANNULA" or "INTRALUMINAL CANNULA" shall both mean the tube with attached seal that is inserted by the intraluminal cannula placement apparatus of the present invention. A SPECIALIZED CANNULA is longer than a CATHETER and has an outside diameter smaller than the interior diameter of a CATHETER.

Description Of The Preferred Embodiments

The present invention provides for the insertion of a specialized cannula through a catheter, which has been previously inserted into a blood vessel, to overcome a constriction or obstruction (such as flexure of the limb). The specialized cannula is longer than the catheter and is sufficiently long to pass beyond the constriction or obstruction that is reducing the flow of blood in the blood vessel in which the catheter is inserted. The outside diameter of the specialized cannula is smaller than the inside diameter of the catheter so that the specialized cannula can be slidingly inserted. However, the inside diameter of the specialized cannula is large enough so that a medically sufficient amount of fluid may pass. Most importantly, the specialized cannula can be inserted without the need to remove the previously inserted catheter. Further, once installed, no part of the specialized cannula extends proximally beyond the end of the previously inserted female catheter hub. These and other features of the invention are described in the following written description and figures.

The intraluminal cannula invention consists of two interrelated components. A specially adapted cannula is provided that may be placed within a previously inserted catheter and which has affixed to one end a seal that provides a fluid-tight secure connection to the previously inserted catheter. The specialized cannula is placed in the previously inserted catheter by the matching intraluminal cannula placement apparatus of the invention.

Figure 1:
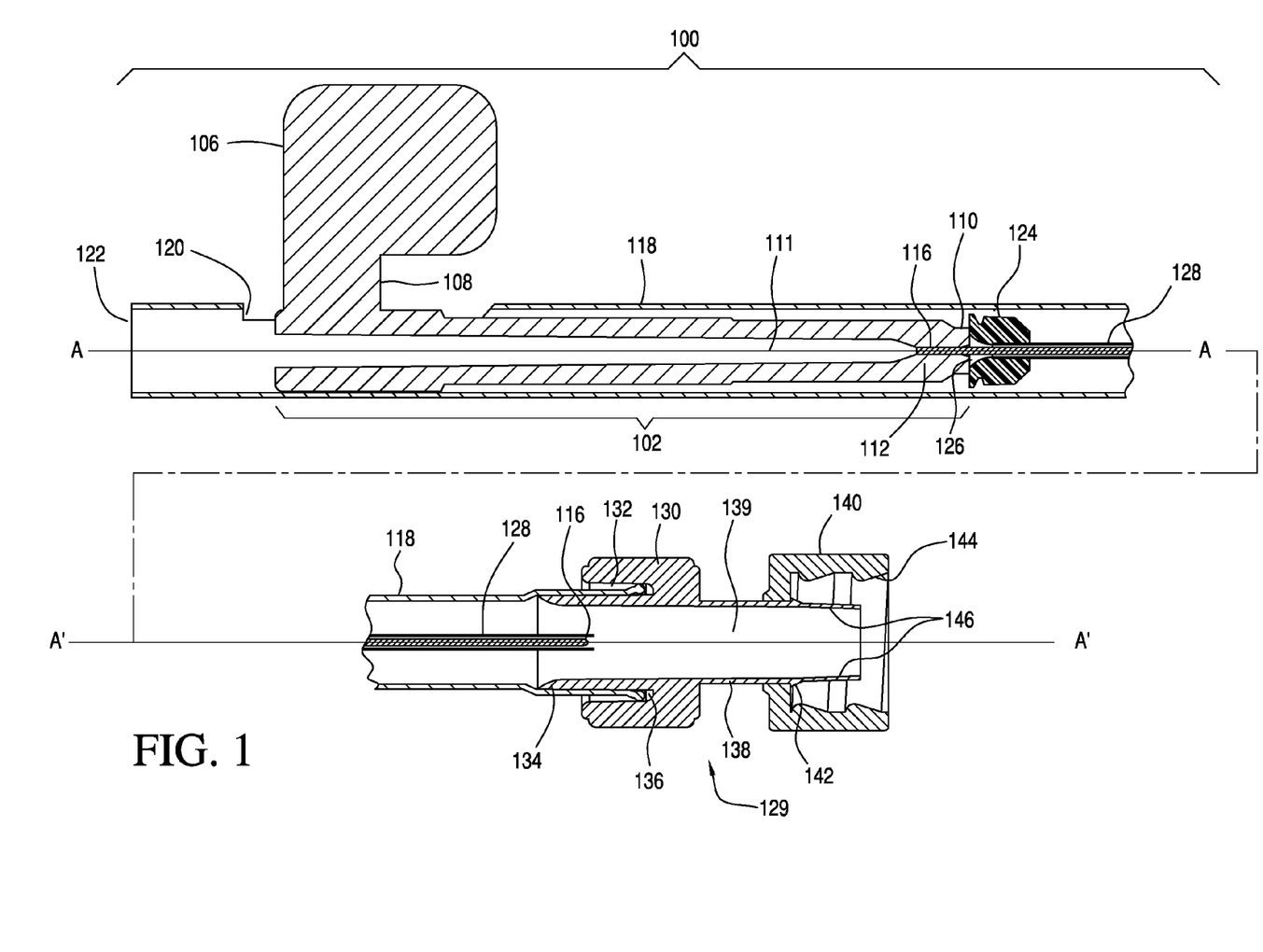
FIG. 1 is a longitudinal cross-sectional view of the intraluminal cannula placement apparatus in its initial retracted position before coupling to a standard I.V. catheter.

Referring now to FIG. 1, the overall construction of the invention can be seen. The specialized cannula and intraluminal cannula placement apparatus 100 of the present invention are shown in longitudinal cross section. A pusher tab 106 protrudes from within tubular protective sheath 118 through opening 120 in sheath 118. Pusher tab 106 is attached to A substantially cylindrical pusher body 102 by connecting support 108. The pusher body 102 has a hollow center 111 and a reduced diameter near its distal end 110 to provide clearance for seal 124 to flex. Located within tubular sheath 118, pusher body 102 has an outside diameter slightly smaller that the interior diameter of tubular sheath 118 so that pusher body 102 may slide freely inside sheath 118. The long axis A-A' of pusher body 102 is substantially aligned with the long axis of sheath 118. Pusher body 102 is shown in its initially retracted position near the proximal end 122 of sheath 118. Flexible supporting rod 116 is attached to the distal end 112 of pusher body 102 centered on the long axis A-A' of pusher body 102 and extends almost to the end of specialized cannula 128. Flexible rod 116 adds rigidity to specialized cannula 128 during its insertion. However, rod 116 is shorter in length than specialized cannula 128 so that it cannot come into contact with a blood vessel wall when specialized cannula 128 is inserted. Rod 116 is also flexible so that it can flex to the contours of the blood vessel wall. A hole 126 in seal 124 provides for slidable engagement of seal 124 around rod 116. Hole 126 has an interior diameter equal to or greater than the outside diameter of supporting rod 116. To form the specialized cannula 128, a flexible cannula 127 is secured to seal 124 within hole 126. The interior diameter of specialized cannula 128 is greater than the outer diameter of rod 116 permitting the specialized cannula to slide over rod 116.

At the distal end of the intraluminal cannula placement apparatus, tubular sheath 118 is secured within circular groove 132 formed by the extensions 134 and body 130 of modified male Luer coupling 129. Tubular sheath 118 is seated at the distal end 136 of circular groove 132. Modified male Luer coupling 129 has a body 130 from which extends tube extension 138. The outer wall at the distal end 146 of tube extension 138 is tapered inwardly and has a reduced thickness from that of an unmodified male Luer coupling. Extensions 134, body 130, and tube extension 138 provide a hollow passageway 139 through modified male Luer coupling 129. Modified male Luer coupling 129 also has a movable locking fastener 140 that slidable engages tube extension 138. Locking fastener 140 is prevented from detaching from tube extension 138 by circular barb 142. Spiral Luer lock fastening threads 144 are located on the interior surface of movable fastener 140.

Figure 2A:
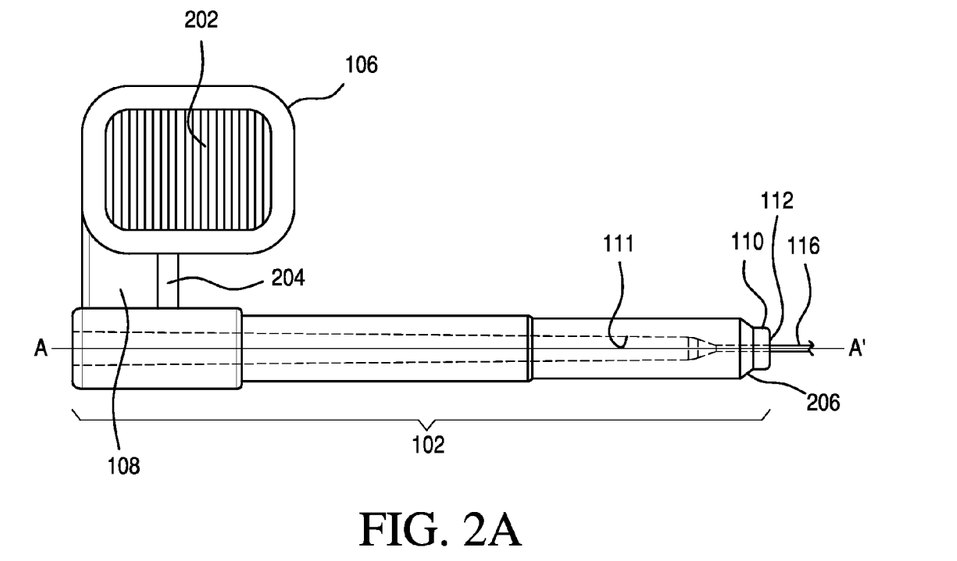
FIG. 2A shows a side view of the pusher.
Figure 2B:
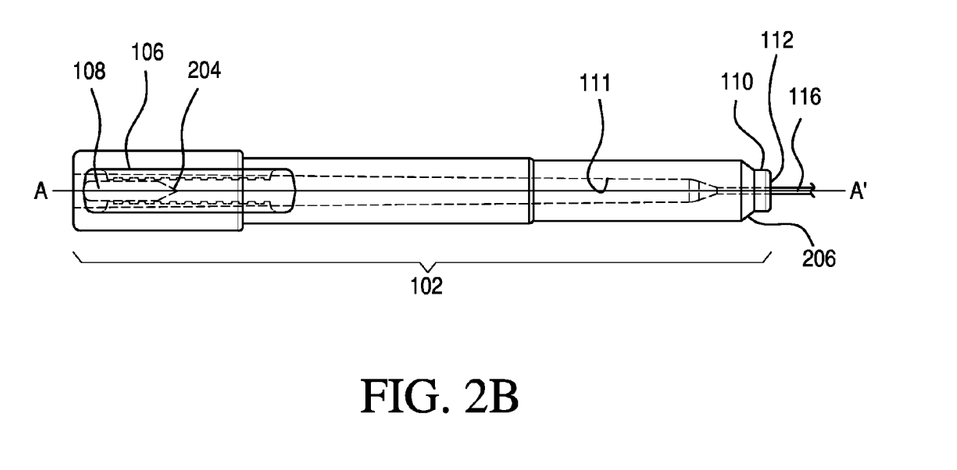
FIG. 2B shows a view of the pusher seen from above.
Figure 8:
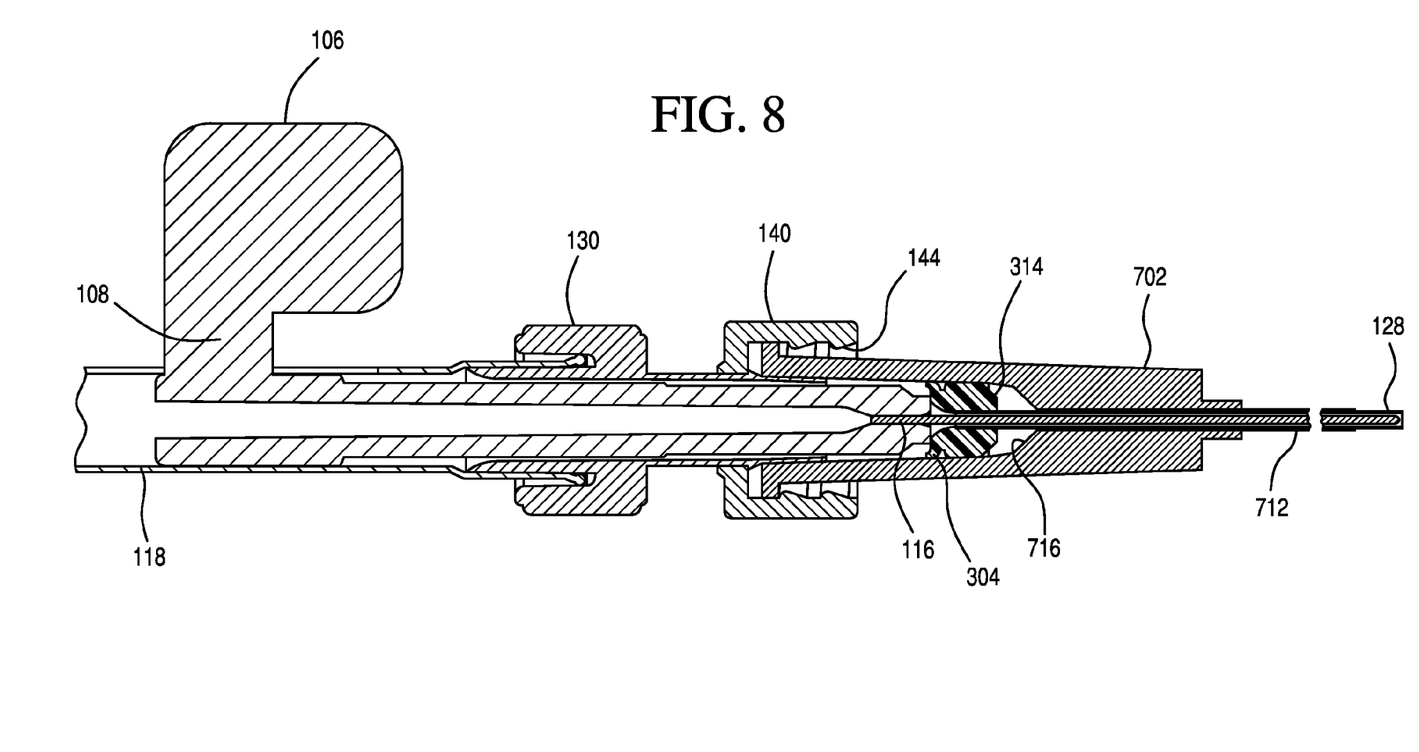
FIG. 8 is a longitudinally cross-sectional view showing the modified locking male Luer coupling of the intraluminal cannula placement apparatus engaging the female locking ring of the female Luer fitting as shown in FIG. 7. Further, the pusher of the intraluminal cannula placement apparatus is shown advanced towards the distal end of the device pushing ahead of it the seal and cannula. The seal is shown just before it makes contact with the distal end of the interior lumen of the female Luer adapter.
Figure 9:
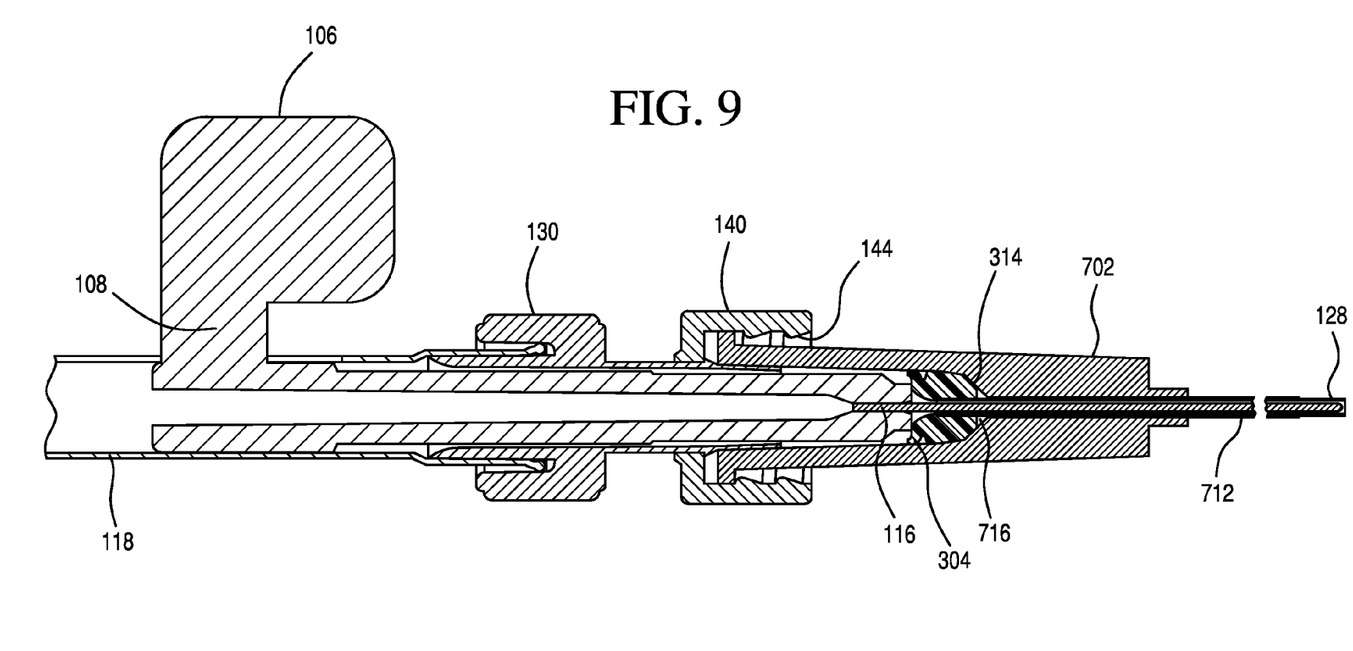
FIG. 9 is similar to FIG. 8 but shows the pusher sufficiently advanced to place the seal in engagement with the distal end of the interior lumen of the female Luer fitting on the standard I.V. catheter hub.

Further details of the construction of the various parts of the invention and their interrelationship can be seen in the following figures. FIG. 2A shows a side view and FIG. 2B shows a top view of pusher 102. The smaller diameter 110 of distal end 206 of pusher body 102 is shown. As noted, the smaller diameter 110 of pusher 102 provides clearance for seal flange 304 to fold backwards towards the proximal end of 102 (as shown in FIGS. 8 and 9). The forward edge 204 of support 108 is beveled to aid in separating the edges of a slot or serrated slot in tubular sheath 118 (not shown) that will be described below. The side 202 of tab 106 is ridged to aid in grasping.

Figure 3A:
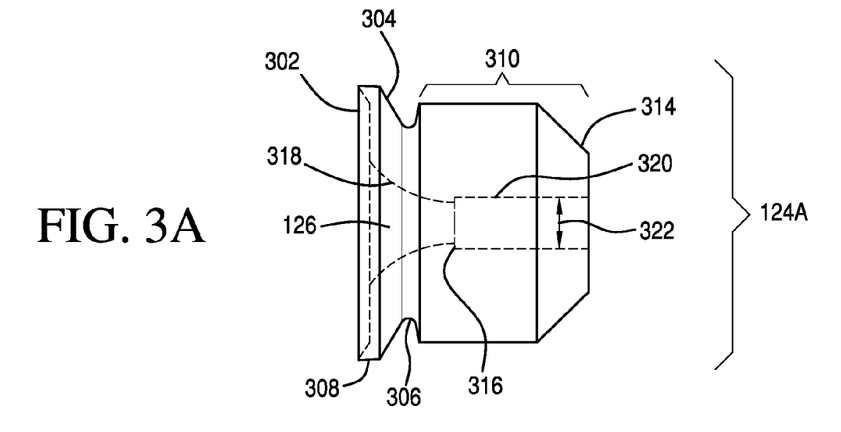
FIG. 3A shows a long nose seal for use on the specialized cannula.
Figure 3B:
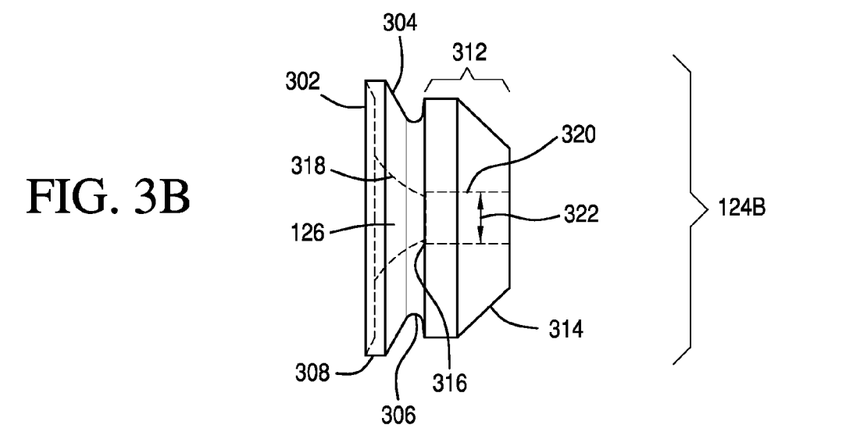
FIG. 3B shows a short nose seal for use on the specialized cannula.
Figure 3C:
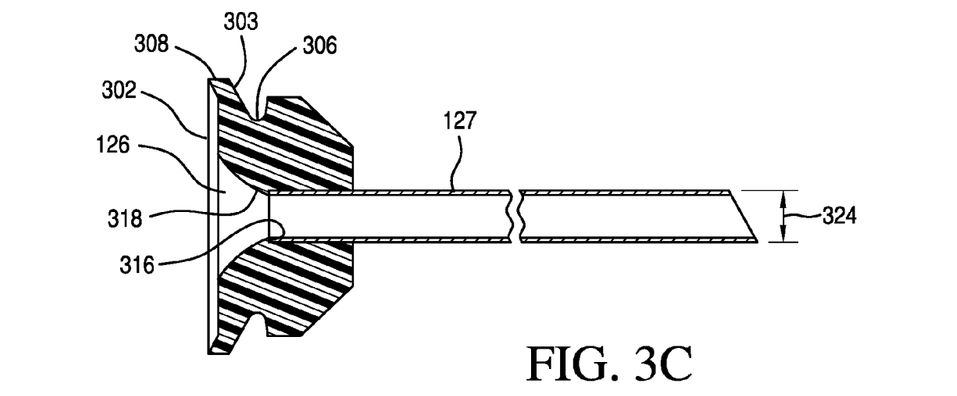
FIG. 3C shows a cross sectional view of a short nose seal with a cannula mounted in the seal.

FIGS. 3A, 3B, and 3C show the construction details of seal 124. The generally conical shape of seal 124 allows seal 124 to pass into lumen 704 of a female catheter hub adapter 702 and seat against the distal end 716 of the lumen 704 as shown in FIG. 9. Both configurations 124A and 124B of seal 124 have a substantially flat proximal surface 302 that is engaged by the distal end 206 of pusher 102. Seals 124A and 124B depicted in FIGS. 3A and 3B differ in the length of the noses 310 and 312 to accommodate differences in the design of the "standard" I.V. catheter hub from different manufacturers. It has been determined through exacting measurement of the available standard Luer female catheter hubs that one or the other of the two seal designs/shapes 124A or 124B will fit all available female catheter hubs. FIG. 3A shows a long nose 310 seal 124A while FIG. 3B shows a short nose 312 seal 124B. The selection of a long nose or short nose seal is determined relative to the dimensions of the standard I.V. catheter hub selected by a practitioner. Other than the length of the nose, the seals are the same and are composed of a flexible material suitable for I.V. exposure. The distal end of the noses 310 and 312 are tapered at 314 to match the tapered wall 716 at the distal end of the lumen of female catheter hub 702. The proximal end 302 of each seal 124A and 124B has a flexible flange 304 formed from an outer rim 308 and groove 306. The diameter of the outer rim 308 is greater than the diameter of either nose 310 or 312 and of lumen 704 of the female catheter hub 702.

During insertion of specialized cannula 128 (as will be described below), the flexible flange 304 folds back (towards its proximal end) to allow seal 124 to pass through the modified male Luer coupling 129 and into the standard female catheter hub 702. Upon insertion of specialized cannula 128 into the standard female catheter hub 702, flange 304 engages the side walls 706 of lumen 704 and, upon complete insertion, surface 314 of seal 124 engages the tapered walls 716 at the distal end of the internal lumen 704 of the standard female catheter hub 702. Engagement of seal surface 314 with lumen surface 716 provides an initial fluid-tight seal. Further, flexible flange 304 expands against the side walls 706 of lumen 704 to create a fluid-tight seal that also permanently anchors seal 124 and specialized cannula 128 within the standard female catheter hub 702.

As can be seen in the cross section of FIG. 3C, seal 124 has a centrally located opening 126 starting with a flared opening 318 at the proximal surface 302. Flared opening 318 extends distally along the longitudinal axis of seal 124 and reduces fluid flow friction maximizing fluid flow into cannula 127. Flared opening 318 decreases in diameter to a diameter less than the outside diameter 324 of cannula 127. Opening 320 through the distal portion of seal 124 is of substantially uniform diameter 322 and sized for the dimensions of the cannula 127 to be attached to the seal. Due to the differences in diameters of tapered opening 318 and cannula opening 320, a stop is formed at 316 (as best send in FIGS. 3A and 3B) against which cannula 127 rests after insertion into hole 320. Cannula 127 is permanently mounted in seal 124 against stop 316. Cannula 127 can be held in place by compression of the seal material, or by means of appropriate cements, or formed by means of injection molding of the seal body 124 around cannula 127 by techniques known to those skilled in the art. The length of specialized cannula 128 is sufficient to extend beyond the site of possible flexural occlusion of a blood vessel when used in a clinical application.

FIGS. 4A-D shows five embodiments of a protective sheath 118. Sheath 118 shields cannula 128 and pusher 102 from contamination during handling and, in conjunction with modified male Luer coupling 129, holds pusher 102 and cannula 128 in alignment with a standard I.V. catheter hub 702 during insertion. Further, the design of sheath 118 reduces the likelihood of blood or bodily fluid contamination of the patient or practitioner during use by containing fluids within sheath 118. Sheath 118 is tubular and substantially cylindrical and is open at both ends. Various embodiments of protective sheath 118 are shown in FIGS. 4A-4E. The internal diameter of sheath 118 is sized to slidingly engage the external diameter of pusher body 102, to permit attachment of the protective sheath 118 to the modified male Luer coupling 129, and to allow longitudinal passage of specialized cannula 128 through sheath 118 and through modified male Luer coupling 129. The length of sheath 118 is adapted to the length of cannula 128 that is to be inserted. During storage, a cap (not shown) may be placed on the distal end of modified malel Luer coupling 129 so that the cannula does not protrude outside the intraluminal cannula placement apparatus before use and sterility is maintained.

FIGS. 4A-4E show perspective views of the embodiments of sheath 118 with longitudinal guide tracks 414 and 416 traversing the wall of sheaths 118. Pusher 102 is advanced manually along tracks 414 or 416. In FIGS. 4A-4D, tracks 414 and 416 do not extend fully to the proximal and distal ends of sheaths 118. The proximal portion 122 of sheath 118 without a track prevents pusher 102 from exiting from the proximal end while the distal portion of sheath 118 without a track allows attachment of sheath 118 in slot 132 in modified male Luer coupling 129. The internal and external diameters of sheath 118 are substantially uniform along its entire length.

Figures 4A, 4B, 4C, 4D, 4E:
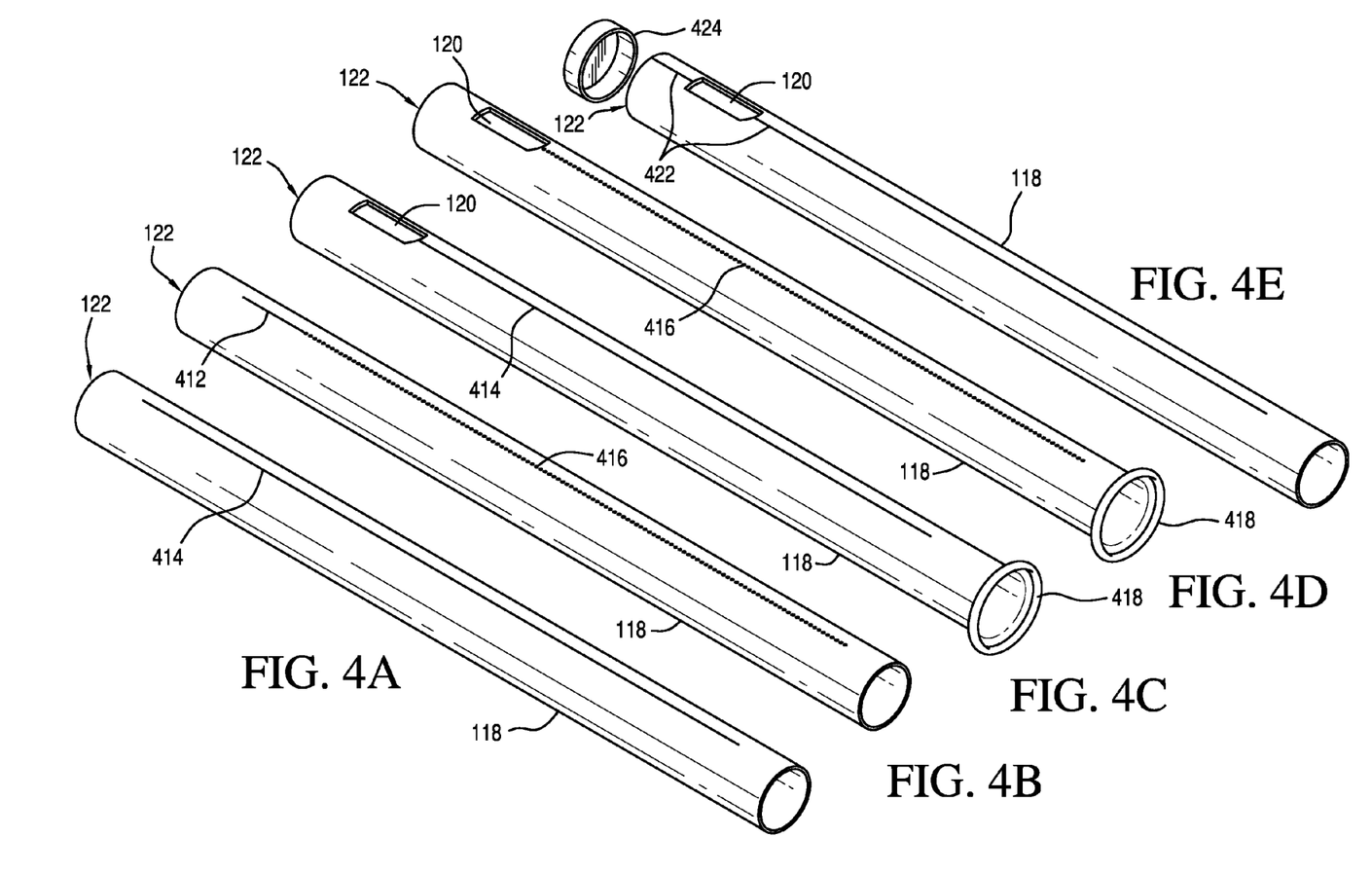
FIGS. 4A, 4B, 4C, 4D, and 4E are perspective drawings of different embodiments of a protective sheath of the intraluminal cannula placement apparatus.

FIG. 4A shows an embodiment in which track 414 is a slit through the wall of sheath 118. Sheath 118 is formed from a material that will allow the forward beveled edge 204 of pusher 102 to separate the wall material to permit advance of pusher 102 from the proximal to distal end of sheath 118 as far as slit 414 will allow.

FIG. 4B shows a second embodiment of sheath 118. This embodiment has a track that is a combination of a proximal slit 412 and a series of spaced perforations 416 along the longitudinal axis and through the wall of sheath 118. The slit 412 additionally holds the pusher support 108 (and therefore pusher 102) at the proximal end 122 of sheath 118 prior to use. In use, the pusher 102 is manually moved distally within the protective sheath; the beveled edge 204 of support 108 cuts/separates the sheath 118 wall along the track of spaced perforations 416 during this action.

FIG. 4C shows a third embodiment of sheath 118 having a distal rolled flange 418 which is used to secure attachment of sheath 118 within slot 132 in modified male Luer coupling 129. Opening 120 at the proximal end of track 414 will accommodate support 108 of pusher 102. Opening 120 and a closed track 414 will restrain pusher 102 at the proximal end 122 of sheath 118 until use. In use, the user grasps tab 106 to advance pusher 102 distally within sheath 118; the beveled edge 204 of support 108 separates the sheath wall during this action.

FIG. 4D shows a fourth embodiment of sheath 118 having a distal rolled flange 418 which is used to secure attachment of sheath 118 within slot 132 in modified male Luer coupling 129. Opening 120 at the proximal end of track 416 will accommodate support 108 of pusher 102. Track 416 is composed of spaced perforations. Opening 120 and a track 416 formed of spaced perforations will restrain pusher 102 at the proximal end 122 of sheath 118 until use. In use, the user will grasp tab 106 to advance pusher 102 distally within sheath 118; the beveled edge 204 of support 108 cuts the sheath wall along track 416 of spaced perforations during this action.

In a preferred embodiment shown in FIG. 4E, slit 422 extends to the proximal end 122 of sheath 118. Pusher 102 may then be easily inserted into sheath 118 at end 122. After pusher 102 has been inserted, a cap 424 is placed over end 122 to both contain pusher 102 and to help seal sheath 118 against contamination. It will be appreciate that the more enclosed sheath 118 is, the less chance there is for contamination of the specialized cannula during insertion and less chance of patient blood leaking and getting on the patient or the practitioner. While those skilled in the art will recognize that there may be other variations of the sheath design not specifically discussed herein, all such variations that perform the same function as those described are considered within the teaching of this patent document.

Sheath 118 can be formed as a unitary item by continuous blow molding or injection molding, and materials such as polyethylene, polyolefin, or other copolymers, may be used. Sheath 118 alternatively may be assembled from more than one part formed separately.

Figure 5A:
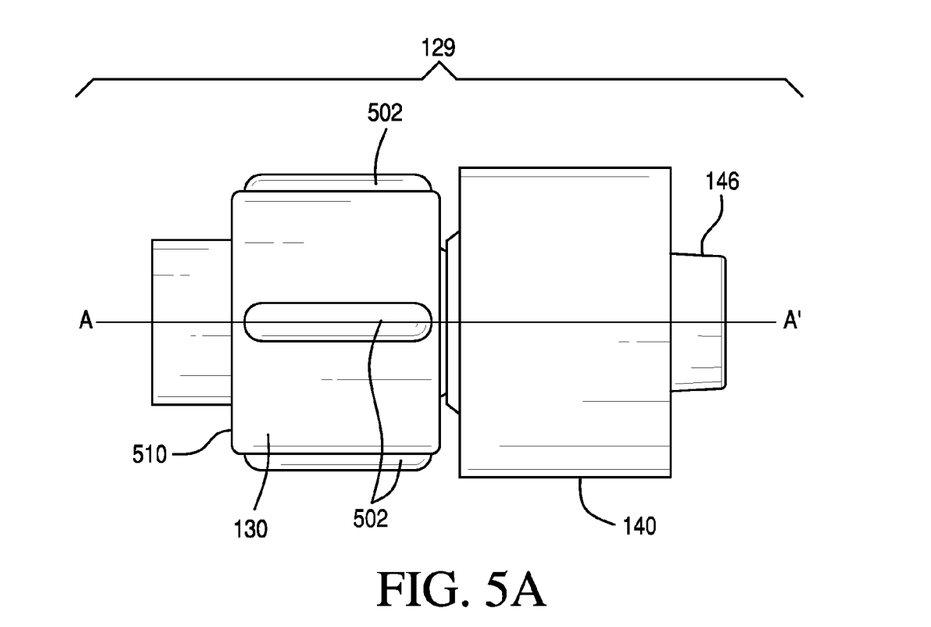
FIG. 5A is a side view of a modified male Luer coupling.
Figure 5B:
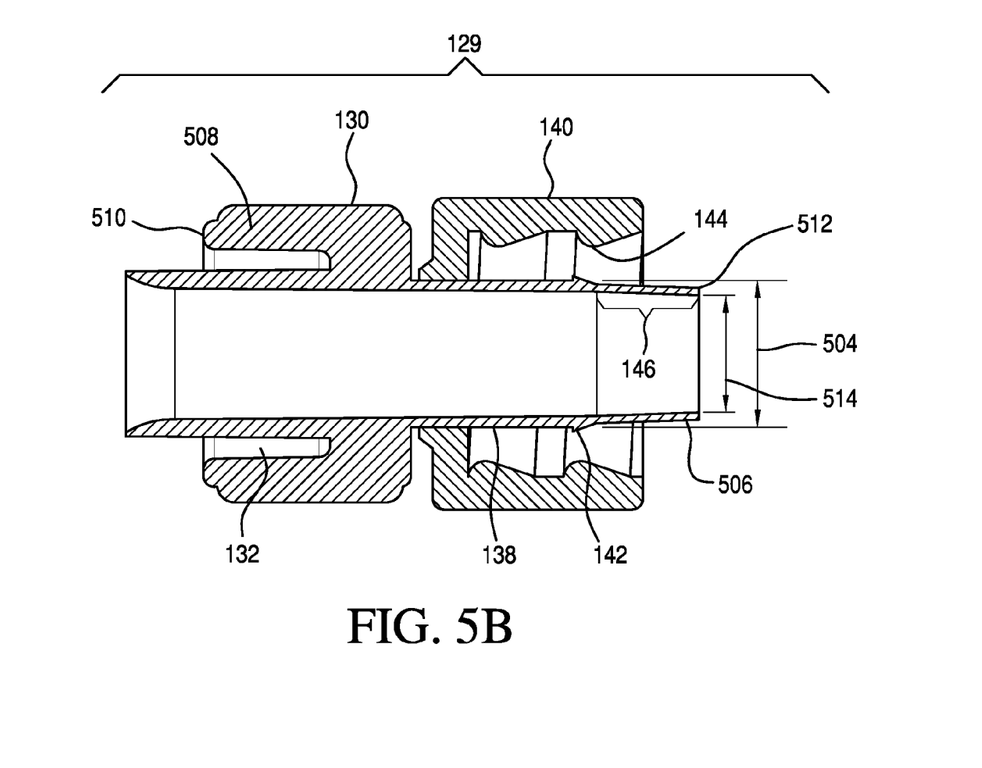
FIG. 5B is a cross sectional view of the modified male Luer coupling.

FIG. 5 shows two views of one embodiment of modified male Luer coupling 129 with distal lock ring 140. FIG. 5A is a schematic view of modified male Luer coupling 129. FIG. 5B is a longitudinal cross-sectional view of the elements of modified male Luer coupling 129. Modified male Luer coupling 129 serves to attach sheath 118 containing pusher body 102 and specialized cannula 128 to the standard female I.V. catheter hub 702. Coupling 129 is referred to as "modified" since it has the following modifications from a standard male Luer adapter. First, coupling 129 has a circular groove 132 within outer wall 508 of its proximal end 510 into which the distal end of sheath 118 is secured. The slot 132 serves to position, stabilize, and protect the junction of the protective sheath 118 and the modified male Luer coupling 129. A second feature of the modified male Luer coupling 129 is a set of protruding ribs 502 on the outer wall of its proximal portion 130 to assist the practitioner in grasping and aligning the intraluminal cannula placement apparatus 100 for proper connection to female Luer adapter.

A third feature of the modified male Luer coupling is the construction of tube extension 138. The distal portion 506 of tube extension 138 has a standard industry taper at 146. The taper at 146 has an initial standard Luer fitting outer diameter 504, but a thinner than standard wall thickness 512. The resulting modified male Luer coupling lumen diameter 514 is thus sufficiently enlarged to allow passage of specialized cannula 128 with seal 124 attached. The tapered distal portion 506 of the modified male Luer coupling 129 fits into the industry standard tapered female Luer hub 702 of the standard I.V. catheter. On the distal portion of modified male Luer coupling 129 there is a rotatable Luer locking fastener 140 that slidingly engages tube extension 138. Proximal to the tapered end 506 of tube extension 138, tube extension 138 has a circular raised barb 142 that prevents Luer locking fastener 140 from disengaging from the distal portion of modified male Luer coupling 129 after its placement during manufacture and during its clinical use. When modified male Luer coupling 129 is fastened with locking fastener 140 to female Luer adapter 702, sheath 118, pusher 102, flexible rod 116, and specialized cannula 128 are all aligned along a common central axis with female Luer adapter 702. As noted above, a standard female Luer end cap (not shown) may be placed onto the distal end of intraluminal cannula placement apparatus 100 to maintain sterility of specialized cannula 128 and to prevent specialized cannula 128 from protruding beyond sheath 118 prematurely.

Figure 6:
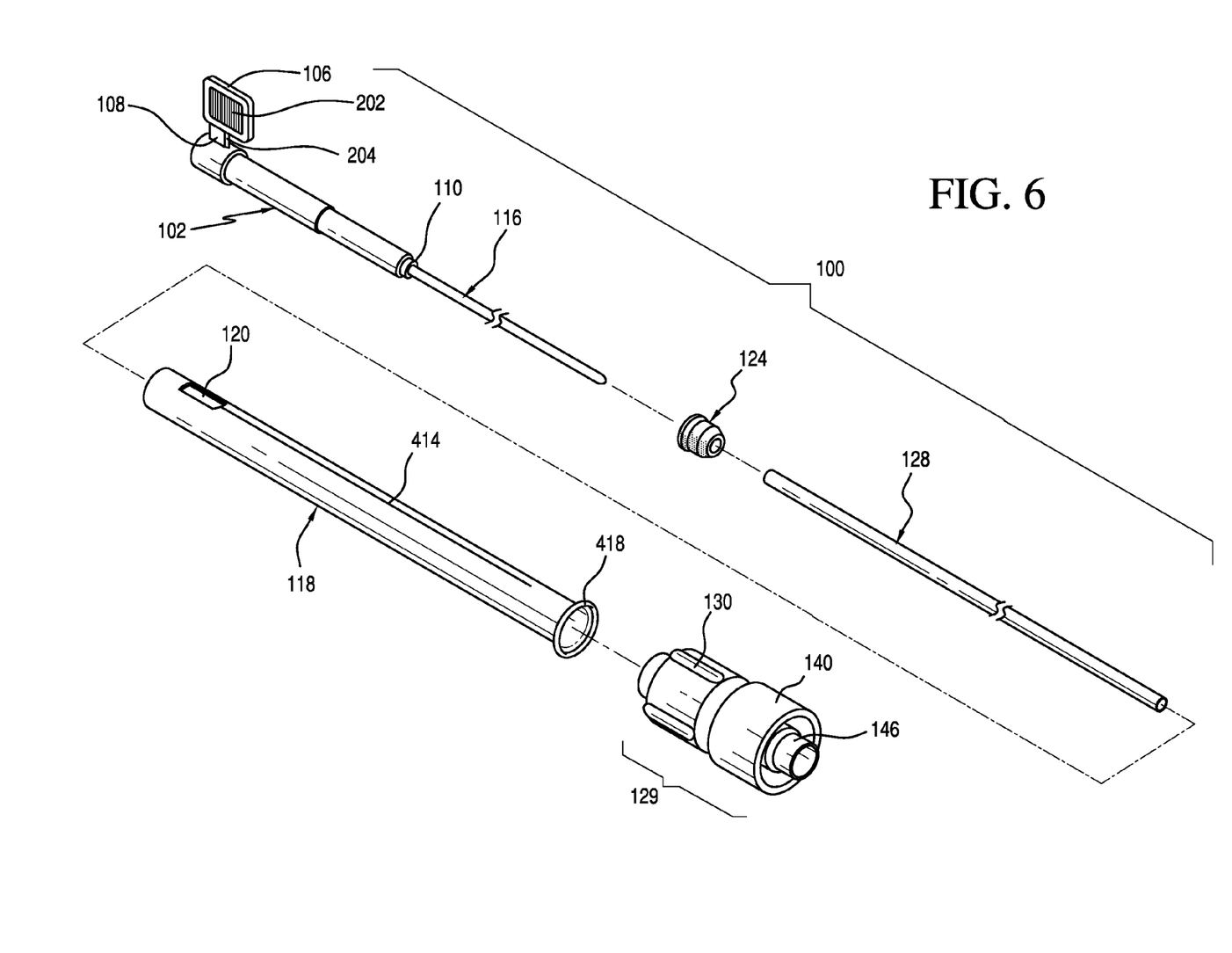
FIG. 6 is a perspective view of an exploded assembly of the intraluminal cannula placement apparatus showing a pusher, a stiffening rod, a seal, a specialized cannula, a sheath, and the modified locking male Luer adapter.

FIG. 6 is an exploded view of the present invention 100 showing the interrelationships of its parts. Embodiments of the inventive device 100 may be supplied in different lengths since the desired length of specialized cannula 128, sheath 118, and flexible rod 116 can vary over a wide range. In most applications, the length is chosen so that the length of specialized cannula 128 (and necessarily the lengths of sheath 118 and flexible rod 116) is sufficient to pass a point of constriction or obstruction in a blood vessel once the specialized cannula is inserted. However, there may be applications where a practitioner wishes to insert a specialized cannula that does not extend past a constriction or obstruction and the present invention permits insertion of such a specialized cannula. In all cases, specialized cannula 128 is inserted through a female catheter hub 702 of a standard I.V. catheter that has been previously inserted into a blood vessel. In the preferred embodiment, pusher 102 is generally cylindrical in shape. However, it can be appreciated that pusher 102 may have any shape (i.e.; a cross section of cross, star, triangle, etc.) that serves to keep flexible rod 116 and specialized cannula 128 centered in sheath 118 and modified male Luer coupling 129. In addition, sheath 118 may have any shaped cross-section along with an appropriately shaped pusher that is compatible with insertion into modified male Luer coupling 129.

All components of the invention are made from sterilizable materials suitable for medial applications, preferably of polyurethane, silicone, or tetrafluoroethylene plastic such as PEBA (polyether block amide polymer, commercially available under the trade name PEBAX® (Autofina Chemicals, Inc., Philadelphia, Pa., USA), ISOPLAST® (engineering thermoplastic polyurethane) or other polyurethanes, nylon, or mixtures thereof suitable to the particular application. The chosen materials must be biocompatible and discourage the generation of a thrombus. The material of specialized cannula 128 may be made from a non-kinking material such as polyurethane. The choice of material from which to manufacture seal 124 is made with at least two properties in mind. Seal 124 has to be flexible enough to pass through modified male Luer coupling 129 and then return to its original shape. Seal 124 must also be firm enough to maintain essentially fluid-tight and secure seating in place at the distal end of the lumen of standard female I.V. catheter hub 702. In the preferred embodiment, the seal is made of polyurethane.

The assembled specialized cannula and intraluminal cannula placement apparatus 100 is preferably packaged within a sterile outer container to maintain sterility of the device after manufacture, shipment, and storage before use. Kits containing the device 100 can further include other instrumentalities, devices, or materials normally associated with the use of an intravenous catheter, including but not limited to tubing, cleaning materials to establish aseptic conditions before insertion of the standard I.V. catheter and/or related components.

Figure 7:
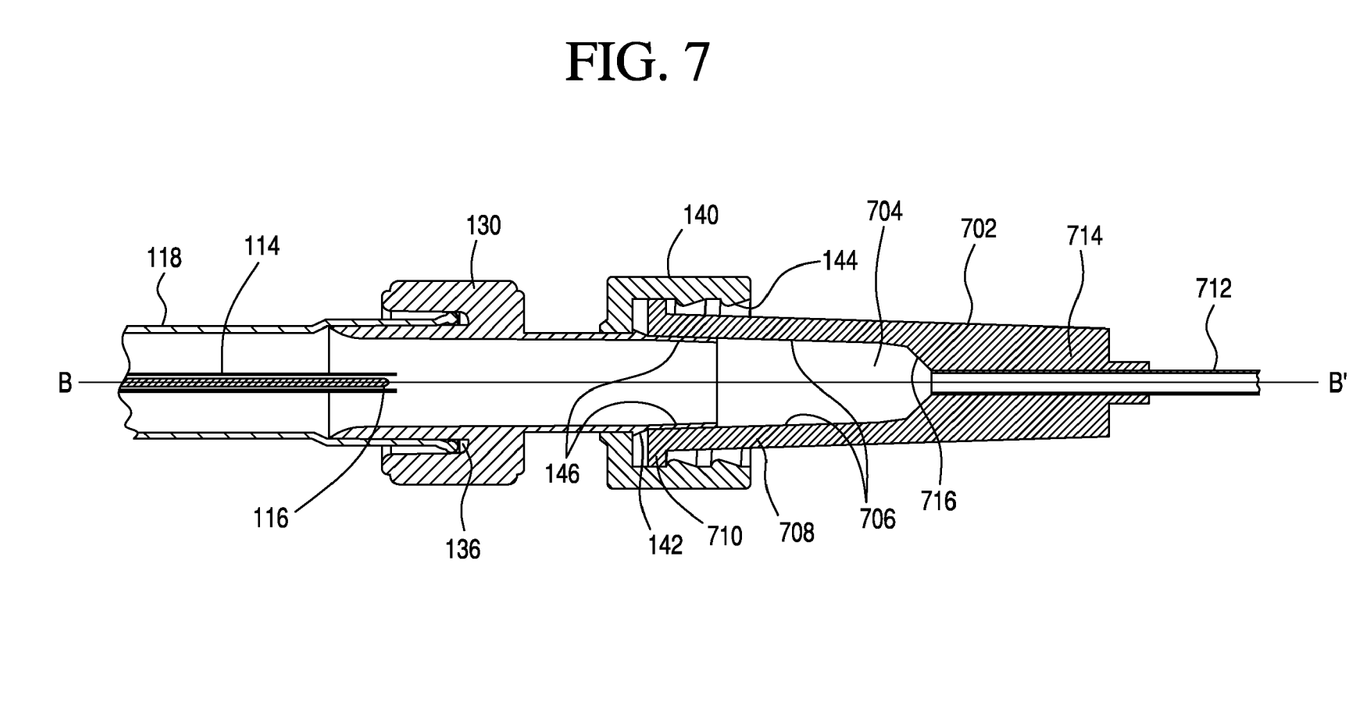
FIG. 7 is a longitudinally cross-sectional view of the modified locking male Luer coupling mounted at the distal end of the intraluminal cannula placement apparatus and engaging the locking ring of the female Luer fitting at the proximal end of an I.V. catheter.

The method of use of the various elements of device 100 will now be described. Once a practitioner has observed a reduction in flow through a previously inserted standard I.V. catheter and has identified the cause of the reduction as a constriction or obstruction of the blood vessel, typically by flexion of a joint distal to the catheter and proximal to the heart, the practitioner can determine the length of specialized cannula 128 needed. The length needed is measured from the female catheter Luer lock hub 702 to a point past the constriction. An appropriately long intraluminal cannula placement apparatus and specialized cannula 100 is chosen. Under aseptic conditions, the practitioner removes any lines or devices secured to the female Luer lock hub 702 of the previously inserted catheter and engages the modified male Luer coupling 129 of intraluminal cannula placement apparatus 100 to female Luer lock hub 702. As shown in FIG. 7, tapered extension 146 of modified male Luer coupling 129 slidingly engages the tapered side walls 706 of lumen 704 of female Luer lock hub 702. The practitioner rotates locking fastener 140 of modified male Luer coupling 129 to engage circular locking tab 710 of female Luer lock hub 702 thereby rigidly coupling intraluminal cannula placement apparatus 100 to female Luer lock hub 702. This coupling aligns apparatus 100 and the female Luer lock hub 702 along a common axis B-B' which is coincident with axis A-A' of apparatus 100 thereby aligning pusher 102, flexible rod 116, and specialized cannula 128 with the catheter 712 of the previously inserted female Luer lock hub 702. FIG. 7 shows the arrangement of the various elements after the practitioner has connected apparatus 100. The intraluminal cannula placement apparatus 100 is usable with most all female Luer lock hubs 702. Female Luer lock hubs 702 are manufactured to a standard specification such as the Terumo Surflo I.V. catheter 22G×1" (Terumo Cardiovascular Systems Corporation, 6200 Jackson Road, Ann Arbor, Mich. 48103-9300, U.S.A.). Commercially available standard I.V. Luer lock catheter hubs are produced by various manufacturers including Abbott, Baxter, B. Braun, and Johnson & Johnson.

Subsequent to coupling, the practitioner grasps pusher tab 106 that protrudes from sheath 118 and advances pusher 102 longitudinally along the length of sheath 118 towards female Luer lock hub 702. As pusher 102 is advanced, the distal end 112 of pusher 102 engages the proximal surface 302 of seal 124 and advances seal 124, flexible rod 116, and specialized cannula 128 towards and into female Luer lock hub 702. Simultaneously, the beveled edge 204 of support 108 follows and separates an opening in guide track 414 or 416 in sheath 118. As pusher 102 is advanced, the alignment along a common central axis insures that flexible rod 116 and specialized cannula 128 enter catheter 712 attached to the female Luer lock hub 702. Specialized cannula 128 is kept from kinking or otherwise distorting as it enters catheter 712 by flexible rod 116. In this manner, the distal end of specialized cannula 128 is advanced longitudinally within sheath 118, through modified male Luer coupling 129, into female Luer lock hub 702, through catheter 712, and into the blood vessel until seal 124 engages the wall 716 at the distal end of the interior lumen 704 of female Luer lock hub 702. FIG. 8 shows specialized cannula 128 inserted into catheter 712 immediately before the distal end 314 of seal 124 engages the walls 716 at the distal end of the interior lumen 704 of female Luer lock hub 702. The flange 304 of seal 124 is shown bent proximally in sealing engagement with the interior walls 706 of Luer lock hub 702.

FIG. 9 shows the distal end 314 of seal 124 fully seated against the wall 716 at the distal end of the interior lumen 704 of female Luer lock hub 702. By engaging the interior walls 706 of lumen 704 of Luer lock hub 702, flange 304 of seal 124 securely holds specialized cannula 128 in place so that specialized cannula 128 cannot be removed without removing catheter 712 (and attached female Luer lock hub 702). This means that any blood clots or fibrin that might accumulate between specialized cannula 128 and catheter 712 will not be stripped off by just removal of specialized cannula 128 to enter the patients blood steam to cause complications.

Once seal 124 is securely in place, flexible rod 116 is withdrawn from female Luer lock hub 702 by reversing the direction of pusher 102, and the intraluminal cannula placement apparatus is disconnected from female Luer lock hub 702 by unscrewing locking fastener 140 of modified male Luer coupling 129. Female Luer lock hub 702 may then be reattached to I.V. supply lines. A major advantage of the use of this invention is that insertion of seal 124 and specialized cannula 128 adds no extracorporeal components to female Luer lock hub 702 that would lengthen the exposed female Luer lock hub 702 or otherwise hinder the normal attachment of fluid lines or other delivery devices to female Luer lock hub 702. The intraluminal cannula placement apparatus is discarded after the specialized cannula is in place.

Figures 10A, 10B:
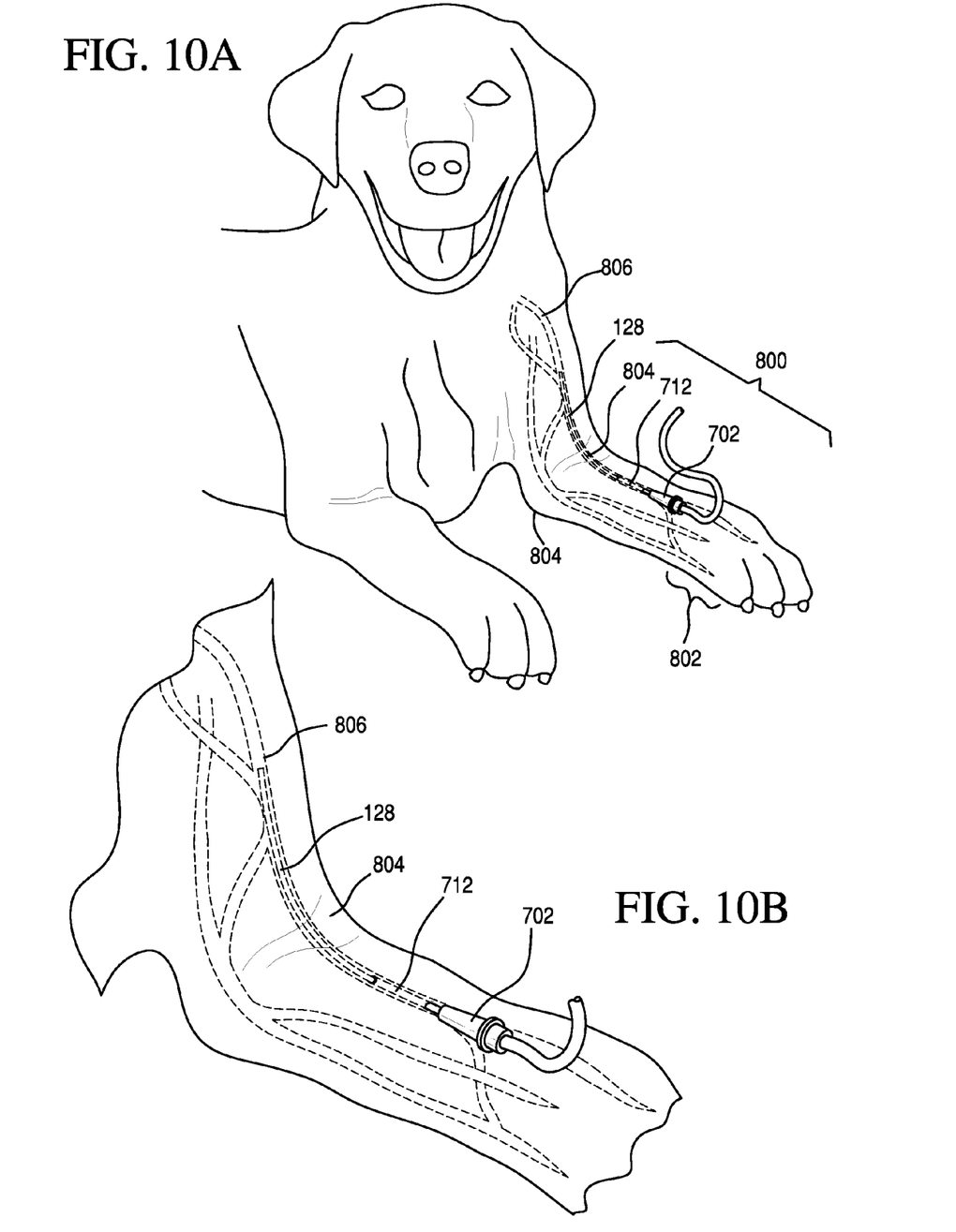
FIGS. 10A and 10B show the placement of an intraluminal cannula in the foreleg of a dog.

FIGS. 10A and 10B show the use of an intraluminal cannula 128 in a veterinary setting after it has been placed in the foreleg 800 of a dog. FIG. 10B is an enlargement of foreleg 800 shown in FIG. 10A. A standard catheter 712 with Luer hub 702 had been inserted just distal to the radial carpal joint 802. The dog's elbow joint is flexed at 804 and may cause obstruction of blood vessel 806. Intraluminal cannula 128 has been positioned through and beyond the point of flexion 804 to provide for the continuous flow of fluids in the previously placed I.V. catheter. The previously inserted female Luer lock hub 702 remains attached to the previously placed catheter 712 within the blood vessel 806. A practitioner determines the length of intraluminal cannula 128 needed to pass beyond the point of obstruction. As noted above, the required length is measured from the female catheter Luer lock hub 702 to a point past the point of obstruction 804. The specialized cannula and intraluminal cannula placement apparatus 100 of the present invention can be scaled to provide intraluminal cannulas of the appropriate length.

Figure 11:
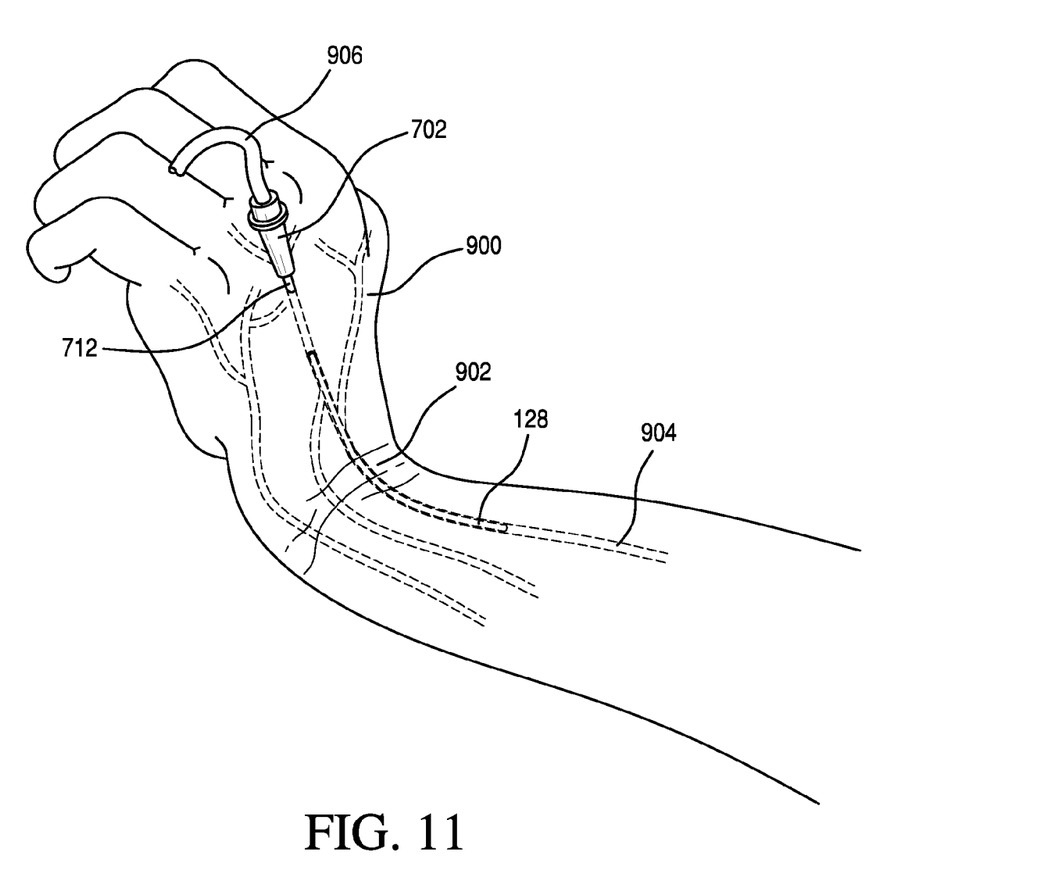
FIG. 11 shows the placement of an intraluminal cannula in a human wrist.

FIG. 11 shows the intraluminal cannula 128 as it may be used for a human. A previously placed catheter 712 with Luer lock hub 702 is shown placed in the back of a human hand 900. The standard catheter 712 is inserted in blood vessel 904. Wrist 902 is shown bent in a manner that normally obstructs the flow of fluids from IV tubing 906 through catheter 712. Intraluminal cannula 128 has been inserted through catheter 712 and passed beyond the point of obstruction at wrist 902.

From the proceeding description of the construction of the cannula placement apparatus and specialized cannula, those skilled in the art will appreciate that variations of construction may be employed without departing from the teachings of the present disclosure, and any such varied embodiments are considered within the scope of this disclosure and the claims appended hereto.

I claim:

1. A intraluminal cannula placement apparatus and specially adapted cannula for placing the cannula into a previously inserted I.V. catheter that has a female Luer connector comprising:
   a) a cannula having proximal and distal ends;
   b) a flexible seal attached to the proximal end of the cannula and shaped to engage the interior of the female Luer connector;
   c) a sheath encasing the cannula and seal and having an interior diameter greater than the outer diameter of the cannula;
   d) a rod having proximal and distal ends and passing through the seal and extending through the interior of the cannula and having an outer diameter less than the interior diameter of the cannula;
   e) a slit in the sheath partially extending along the length of the sheath;
   f) a pusher comprising:
      i) an elongated body attached to the proximal end of the rod having an exterior diameter less than the interior diameter of the sheath;
      ii) a stem attached to the body and extending through the slit in the sheath;
      iii) a tab attached to the stem on the outside of the sheath; and
   g) a modified male Luer coupling at the distal end of the sheath;
   wherein the modified male Luer coupling lockingly engages the female Luer connector thereby permitting the pusher to engage the seal to advance the cannula into and through the I.V. catheter until the flexible seal compressively engages the interior wall of the female Luer connector thereby securing the cannula in place and preventing leakage.

2. The intraluminal cannula placement apparatus of claim 1 in which the sheath is flexible.

3. The intraluminal cannula placement apparatus of claim 1 which all elements are sterilizable.

4. The intraluminal cannula placement apparatus of claim 1 in which the sheath is plastic.

5. The intraluminal cannula placement apparatus of claim 1 in which the slit may extend along the sheath to the proximal but not the distal end of the sheath.

6. The intraluminal cannula placement apparatus of claim 1 in which the rod is flexible.

7. The intraluminal cannula placement apparatus of claim 6 in which the rod is made of wire.

8. The intraluminal cannula placement apparatus of claim 1 in which the length of the cannula is sufficiently long to extend into and beyond the distal tip of the previously placed standard I.V. catheter.

9. The intraluminal cannula placement apparatus of claim 1 in which the cannula is permanently attached to the center of the flexible seal.

10. The intraluminal cannula placement apparatus of claim 1 in which an end cap seals the sheath.

11. A method for placing a cannula into and through a previously inserted I.V. catheter having a female Luer connector comprising the steps of:
   a) fastening to the female Luer fitting of the inserted I.V. catheter an intraluminal cannula placement apparatus comprising:
      1) a cannula having proximal and distal ends;
      2) a flexible seal attached to the proximal end of the cannula and shaped to engage the interior of the female Luer connector;
      3) a sheath encasing the cannula and seal and having an interior diameter greater than the outer diameter of the cannula;
      4) a rod having proximal and distal ends and passing through the seal and extending through the interior of the cannula and having an outer diameter less than the interior diameter of the cannula;
      5) a slit in the sheath partially extending along the length of the sheath;

6) a pusher comprising:
   (a) an elongated body attached to the proximal end of the rod having an exterior diameter less than the interior diameter of the sheath;
   (b) a stem attached to the body and extending through the slit in the sheath;
   (c) a tab attached to the stem on the outside of the sheath; and
7) a modified male Luer coupling at the proximal end of the sheath;
b) advancing the pusher towards the distal end of the intraluminal cannula placement apparatus to engage the seal and advance the cannula into and through the I.V. catheter; and
c) compressively engaging the seal against the interior wall of the female Luer connector thereby securing the cannula in place and preventing backflow of blood into the I.V. catheter and the intraluminal cannula placement apparatus.

12. The method of claim 11 wherein the sheath is flexible.
13. The method of claim 11 in which all elements are sterilizable.
14. The method of claim 11 wherein the sheath is plastic.
15. The method of claim 11 in which the slit in the intraluminal cannula placement apparatus may extend along the sheath to the proximal but not the distal end of the sheath.
16. The method of claim 11 wherein the rod is flexible.
17. The method of claim 16 wherein the flexible rod running through the cannula has an outer diameter less than the interior diameter of the catheter.
18. The method of claim 16 wherein the rod is made of wire.
19. The method of claim 11 wherein the modified male Luer coupling of the intraluminal cannula placement apparatus is turned to lock onto the female Luer connector of the previously inserted I.V. catheter.
20. The method of claim 11 in which the cannula is permanently attached to the center of the flexible seal.
21. The method of claim 11 in which an end cap seals the sheath.
22. A method to prevent potential blockage of an inserted I.V. catheter caused by constriction of a blood vessel and obstruction to blood flow due to limb flexure or extension of a joint by extending through the inserted I.V. catheter a cannula sufficiently long to pass the point of constriction and obstruction comprising the steps of:
   a) fastening to the female Luer fitting of the inserted I.V. catheter an intraluminal cannula placement apparatus comprising:
     1) a cannula having proximal and distal ends;
     2) a flexible seal attached to the proximal end of the cannula and shaped to engage the interior of the female Luer connector;
     3) a sheath encasing the cannula and seal and having an interior diameter greater than the outer diameter of the cannula;
     4) a rod having proximal and distal ends and passing through the seal and extending through the interior of the cannula and having an outer diameter less than the interior diameter of the cannula;
     5) a slit in the sheath partially extending along the length of the sheath;
     6) a pusher comprising:
        (a) an elongated body attached to the proximal end of the rod having an exterior diameter less than the interior diameter of the sheath;
        (b) a stem attached to the body and extending through a slit in the sheath;
        (c) a tab attached to the stem on the outside of the sheath; and
     7) a modified male Luer coupling at the distal end of the sheath;
   b) advancing the pusher towards the distal end of the intraluminal cannula placement apparatus to engage the seal and advance the cannula into and through the I.V. catheter; and
   c) compressively engaging the seal against the interior wall of the female Luer connector thereby securing the cannula in place and preventing backflow of blood into the I.V. catheter and the intraluminal cannula placement apparatus.

23. The method of claim 22 wherein the sheath is flexible.
24. The method of claim 22 wherein all elements are sterilizable.
25. The method of claim 22 wherein the sheath is plastic.
26. The method of claim 22 in which the slit in the intraluminal cannula placement apparatus may extend along the sheath to the proximal but not the distal end of the sheath.
27. The method of claim 22 wherein the rod is flexible.
28. The method of claim 22 wherein the flexible rod running through the cannula has an outer diameter less than the interior diameter of the cannula.
29. The method of claim 22 wherein the rod is made of wire.
30. The method of claim 22 wherein the modified male Luer connector of the intraluminal cannula placement apparatus is turned to lock onto the female Luer connector of the previously inserted I.V. catheter.
31. The method of claim 22 in which the cannula is permanently attached to the center of the flexible seal.
32. The method of claim 22 in which an end cap seals the sheath.

* * * * *